US00PP19603P2

(12) United States Plant Patent
Verschoor

(10) Patent No.: US PP19,603 P2
(45) Date of Patent: Dec. 30, 2008

(54) PHLOX PLANT NAMED 'COSMOPOLITAN'

(50) Latin Name: *Phlox paniculata*
Varietal Denomination: Cosmopolitan

(75) Inventor: Jan Verschoor, Haarlem (NL)

(73) Assignee: Witteman & Co, Hillegom (NL)

( * ) Notice: Subject to any disclaimer, the term of this patent is extended or adjusted under 35 U.S.C. 154(b) by 0 days.

(21) Appl. No.: 11/985,903

(22) Filed: Nov. 19, 2007

(51) Int. Cl.
*A01H 5/00* (2006.01)

(52) U.S. Cl. ..... Plt./320
(58) Field of Classification Search ..... Plt./320
See application file for complete search history.

*Primary Examiner*—Annette H Para
*Assistant Examiner*—S. B. McCormick Ewoldt
(74) *Attorney, Agent, or Firm*—Jondle & Associates, P.C.

(57) ABSTRACT

A new phlox plant particularly distinguished by hot pink flower color, compact plant habit, healthy foliage and good mildew resistance, is disclosed.

2 Drawing Sheets

Genus and species: *Phlox paniculata.*
Variety denomination: 'Cosmopolitan'

BACKGROUND OF THE NEW PLANT

The present invention comprises a new and distinct cultivar of phlox, botanically known as *Phlox paniculata,* and hereinafter referred to by the cultivar name 'Cosmopolitan'. The new cultivar originated from an open pollination in 2005 in Haarlem, The Netherlands between unknown male and female *Phlox paniculata* plants.

The new cultivar was selected from the results of the open pollination in 2006 in Haarlem, The Netherlands and has been asexually reproduced through two generations by vegetative cuttings in Haarlem, The Netherlands since that time. The present invention has been found to retain its distinctive characteristics through successive asexual propagations.

SUMMARY OF THE INVENTION

The following are the most outstanding and distinguishing characteristics of this new cultivar when grown under normal horticultural practices in Haarlem, The Netherlands.

1. Hot pink flower color;
2. Very compact habit;
3. Healthy foliage; and
4. Good mildew resistance.

DESCRIPTION OF PHOTOGRAPHS

This new phlox plant is illustrated by the accompanying photographs which show blooms and foliage of the plant in full color, the colors shown being as true as can be reasonably obtained by conventional photographic procedures. The photographs are of a 2 year-old plant grown in a greenhouse in Haarlem, The Netherlands.

DESCRIPTION OF THE NEW CULTIVAR

Figure 1:
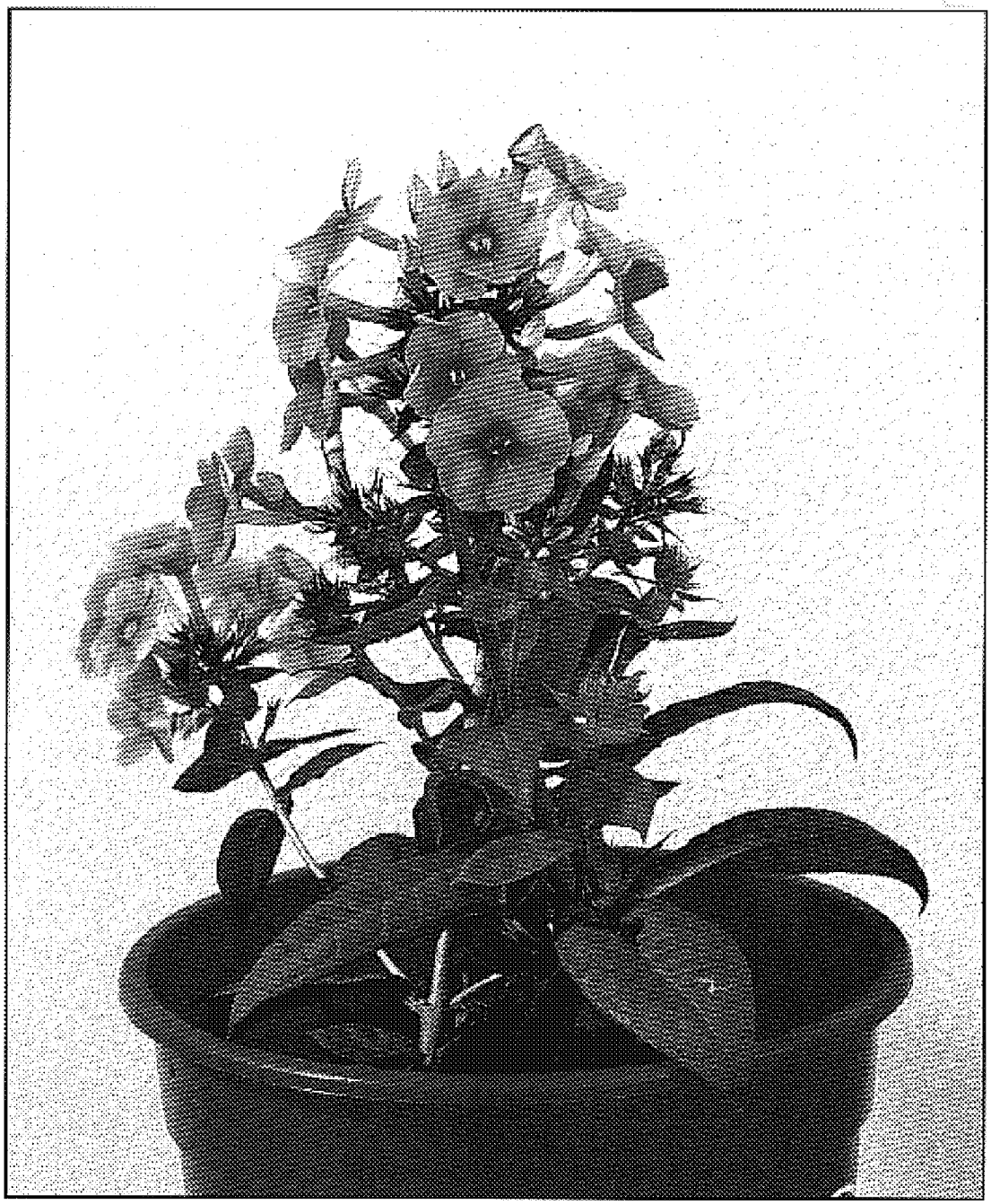
FIG. 1 shows the overall plant habit, including blooms, buds and foliage.
Figure 2:
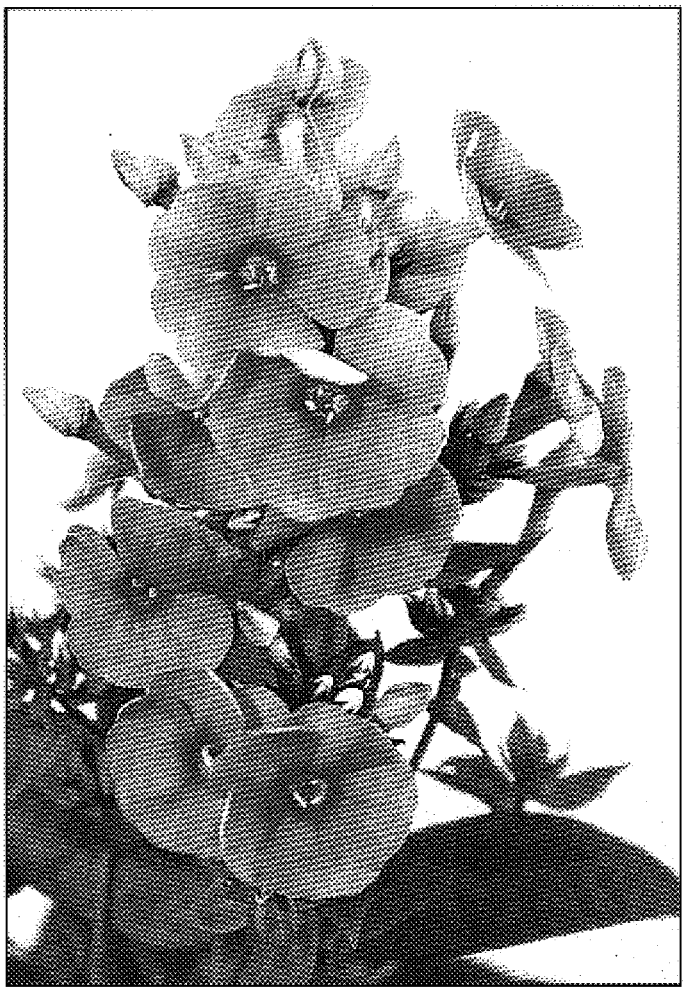
FIG. 2 shows a mature flower.
Figure 3:
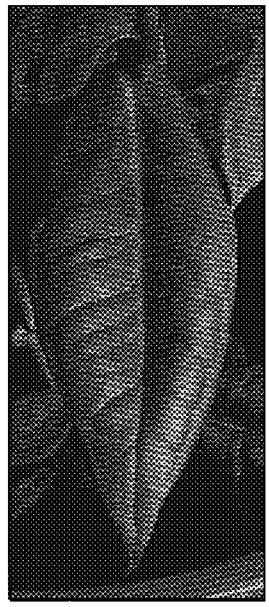
FIG. 3 shows a mature leaf of the plant.

The following detailed description sets forth the distinctive characteristics of 'Cosmopolitan'. The data which define these characteristics were collected from asexual reproductions carried out in Haarlem, The Netherlands. The plant history was taken in August on 1 year old plants which were planted and grown outdoors in daytime temperatures between 14° C. and 32° C., and nighttime temperatures between 5° C. and 15° C. No pinchings, growth retardants or photoperiodic treatments were used. Observations were made when the plants were in natural outdoor light. Color reference primarily to the R.H.S. Colour Chart of The Royal Horticultural Society of London (R.H.S.) (2001).

DETAILED BOTANICAL DESCRIPTION

Classification:
- *Family.*—Polemoniaceae.
- *Botanical.*—*Phlox paniculata.*
- *Common name.*—Phlox.

Parentage:
- *Female parent.*—Unknown.
- *Male parent.*—Unknown.

Growth:
- *Form.*—Herbaceous perennial.
- *Habit.*—Upright, moderate to low vigor.
- *Shape.*—Broad inverted triangle.
- *Height* (*measured from the top of the soil*).—25.8 cm.
- *Diameter.*—22.1 cm.
- *Growth rate.*—8.0 cm per month.
- *Time to produce a finished flowering plant.*—25 weeks from rooted cutting for a 1.5 liter container.
- *High temperature tolerance.*—Tolerant to at least 35° C.
- *Lower temperature tolerance.*—Hardy to USDA Zone 4.
- *Roots.*—White, thin, fibrous, sparse, freely branching.

Branches:
- *Habit.*—Moderate; basal branching.
- *Number of branches.*—1 flowering stem.

Stems:
- *Description.*—Round, glaborous, slightly glossy.
- *Aspect.*—Rounded.

*Color.*—Between RHS 144A (Yellow-green) to RHS 144B (Yellow-green).
*Diameter.*—0.3 cm.
*Stem length* (*excluding inflorescence*).—15.2 cm.
*Internode length.*—2.0 cm.
*Strength.*—Strong.
*Pubescence.*—Absent.

Leaves:
*Arrangement.*—Opposite, single.
*Quantity of leaves* (*per lateral branch*).—14.
*Durability to stress.*—High.
*Shape.*—Elliptic.
*Apex.*—Apiculate.
*Base.*—Truncate to obtuse.
*Color* (*mature leaves*).—Upper surface: RHS 137A (Green). Lower surface: RHS 138B (Green).
*Color* (*immature leaves*).—Upper surface: RHS 143A (Green). Lower surface: Between RHS 143C (Green) to RHS 144A (Yellow-green).
*Margin.*—Revolute, very short, fine serrate (approx. 30 teeth per cm).
*Size.*—Length: 9.6 cm. Width: 3.9 cm.
*Texture* (*upper surface*).—Smooth, glabrous.
*Pubescence.*—Absent.
*Venation.*—Type: Pinnate. Color: Upper surface: RHS 145A (Yellow-green). Lower surface: RHS 145C (Yellow-green).
*Petiole.*—Shape: V-shaped. Length: 0.3 cm. Width: 0.5 cm. Height: 0.25 cm. Color (Both surfaces): Between RHS 145B (Yellow-green) to RHS 145C (Yellow-green).

Flower Buds:
*Color.*—RHS 75C (Purple); towards the tip between RHS 75A (Darker purple) to RHS 75B (Darker purple); lower half between RHS 146C to RHS 146D (Yellow-green); flushed with color between RHS 186B to RHS 186C (Greyed-purple).
*Shape.*—Narrow obovate.
*Size.*—Length: 2.2 cm. Diameter: 0.5 cm.
*Rate of opening.*—Open approximately 4 days.

Inflorescence:
*Blooming habit.*—Continuous during natural flowering season.
*Inflorescence type.*—Self-cleaning, compound terminal panicle.
*Natural flowering season.*—Summer to late summer (July to September).
*Height.*—12.1 cm.
*Width.*—12.2 cm.
*Fragrance.*—Moderate, sweet; typical *Phlox paniculata* scent.
*Quantity of flowers per inflorescence.*—100.
*Quantity of flower buds per lateral stem.*—25.
*Quantity of flower buds per lateral stem.*—75.
*Quantity of flower buds per plant.*—100.
*Rate of flower opening.*—Approximately 25% of the flowers at any stage.
*Flower longevity on plant.*—10 days.
*Flower longevity as a cut flower.*—10 days.

Peduncle:
*Color.*—Between RHS 144A (Yellow-green) to RHS 144B (Yellow-green).
*Length.*—Primary: 8.7 cm. Secondary: 3.4 cm.
*Diameter.*—Primary: 0.25 cm. Secondary: 0.15 cm.
*Angle.*—Primary peduncles average angle is 0° (straight upright), secondary peduncles average angle is 40°.
*Strength.*—Strong.

Pedicel:
*Color.*—RHS 144B (Yellow-green).
*Length.*—0.4 cm.
*Diameter.*—0.1 cm.
*Angle.*—Average angle 30° (0° to 60°) (0° equals straight on top of the peduncle).
*Strength.*—Strong.

Florets:
*Type.*—Single.
*Shape.*—Salverform.
*Aspect.*—Upright and outward.
*Fragrance.*—Moderate, sweet; typical *Phlox paniculata* scent.
*Size.*—Height (flower depth): 2.7 cm. Diameter: 3.4 cm.
*Petals.*—Arrangement: Rotate. Shape: Spathulate, the lower 60% fused into a tube. Appearance: Dull, smooth. Number: 5. Size: Length: 3.5 cm (lower 2.2 cm fused into a tube). Width: 1.9 cm. Apex: Rounded. Margin: Entire. Color (when opening): Upper surface: RHS 73A (Red-purple); base of free part RHS N66A (Red-purple); tube RHS 64D (Red-purple). Lower surface: Between RHS N74C to RHS N74D (Red-purple); tube RHS 63C (Red-purple). Color (fully opened): Upper surface: Between RHS 73A to RHS N74B (Red-purple); base of free part between RHS N66A to RHS N74A. (Red-purple); tube RHS 64D (Red-purple). Lower surface: Between RHS N74C to RHS N74D (Red-purple) tube RHS 63C (Red-purple). Color fading to: RHS N78C (Purple). Texture (both surfaces): Smooth.

Calyx:
*Shape.*—Campanulate.
*Length.*—0.9 cm.
*Diameter.*—0.4 cm.
*Sepals.*—Arrangement: Rotate. Appearance: Smooth, dull. Number: 5. Shape: Linear. Apex: Narrow apiculate. Base: Lower 45% fused. Margin: Entire. Size: Length: 0.9 cm. Width: 0.2 cm. Color (mature): Upper surface: RHS 145A (Yellow-green); flushed with color between RHS 147A (Dark yellow-green) to RHS N200A (Brown). Lower surface: RHS 145A (Yellow-green); flushed with color between RHS 147A (Dark yellow-green) to RHS N200A (Brown). Color (immature): Upper surface: RHS 145A (Yellow-green); flushed with color between RHS 147A (Dark yellow-green) to RHS N200A (Brown). Lower surface: RHS 145A (Yellow-green); flushed with color between RHS 147A (Dark yellow-green) to RHS N200A (Brown).

Reproductive organs:
*Stamens.*—Quantity: 5 Anther: Shape: Basifixed, oblong; filament implanted in petal. Length: 0.3 cm. Length of filament: 0.1 cm. Color: RHS 4D (Yellow).
*Pollen.*—Amount: Moderate. Color: RHS 4C (Yellow).
*Pistil.*—Quantity: 1. Length: 1.8 cm.
*Style.*—Length: 1.7 cm. Color: RHS 146D (Yellow-green).
*Stigma.*—Shape: Cleft (3-parted). Color: Between RHS 150C (Yellow-green) to RHS 150D (Yellow-green).
*Ovary color.*—RHS 143A (Green).

Fruit and Seed Set: No fruit or seeds have been detected to date.

Disease and insect resistance: No particular resistance or susceptibility to diseases or insects noted to date.

COMPARISON WITH COMMERCIAL CULTIVARS

'Cosmopolitan' differs from the commercial *Phlox Paniculata* variety 'Bright Eyes' (unpatented), by having healthier foliage with thicker stems and a sturdier plant than 'Bright Eyes'. Additionally, 'Cosmopolitan' has more compact plant habit with a warmer color than 'Bright Eyes'.

I claim:

1. A new and distinct cultivar of phlox plant as shown and described herein.

* * * * *